(12) United States Patent
Twerdochlib

(10) Patent No.: US 7,123,031 B2
(45) Date of Patent: Oct. 17, 2006

(54) SYSTEM FOR ON-LINE ASSESSMENT OF THE CONDITION OF THERMAL COATING ON A TURBINE VANE

(75) Inventor: Michael Twerdochlib, Oviedo, FL (US)

(73) Assignee: Siemens Power Generation, Inc., Orlando, FL (US)

( * ) Notice: Subject to any disclaimer, the term of this patent is extended or adjusted under 35 U.S.C. 154(b) by 0 days.

(21) Appl. No.: 11/018,771

(22) Filed: Dec. 20, 2004

(65) Prior Publication Data

US 2006/0132149 A1 Jun. 22, 2006

(51) Int. Cl.
*G01R 27/08* (2006.01)
*G01N 27/00* (2006.01)

(52) U.S. Cl. ..................... 324/693; 324/71.2
(58) Field of Classification Search ............... 324/693, 324/691, 649, 600, 667, 378, 664, 421, 525, 324/158.1, 76.11, 71.1, 715, 716, 718, 722, 324/724, 71.2; 342/118; 340/679, 680
See application file for complete search history.

(56) References Cited

U.S. PATENT DOCUMENTS

| | | | |
|---|---|---|---|
| 6,040,694 A * | 3/2000 | Becker ...................... 324/230 |
| 6,251,978 B1 | 6/2001 | McCullough | |
| 6,402,093 B1 * | 6/2002 | Wang ..................... 244/134 R |
| 6,512,379 B1 | 1/2003 | Harrold et al. | |
| 6,644,917 B1 | 11/2003 | Zhao et al. | |
| 6,730,918 B1 | 5/2004 | Srivastava et al. | |
| 6,756,908 B1 * | 6/2004 | Gass et al. .................. 340/679 |
| 6,885,006 B1 * | 4/2005 | Harrold et al. ............. 250/372 |
| 6,979,991 B1 * | 12/2005 | Burns et al. ................ 324/71.1 |
| 2003/0115941 A1 | 6/2003 | Srivastava et al. | |
| 2003/0127602 A1 | 7/2003 | Harrold et al. | |
| 2003/0193331 A1 | 10/2003 | Nath et al. | |
| 2004/0096314 A1 | 5/2004 | Kool et al. | |
| 2004/0101022 A1 | 5/2004 | Hardwicke et al. | |
| 2004/0114666 A1 | 6/2004 | Hardwicke et al. | |
| 2005/0274611 A1 * | 12/2005 | Schlichting ................. 204/401 |

* cited by examiner

*Primary Examiner*—Anjan Deb
*Assistant Examiner*—Hoai-An D. Nguyen

(57) ABSTRACT

Aspects of the invention relate to a system for assessing the condition of a thermal barrier coating on a turbine vane during engine operation. According to embodiments of the invention, one or more wires can be passed along the airfoil portion of the vane. The wires can extend over, within, or beneath the thermal coating. An electrical current can be passed along the wires, and electrical resistance can be measured across the wires. Thus, if a portion of the thermal coating becomes damaged, then the wires located in that area may break. A disconnect in the wires can lead to an increase in resistance across the wires, which can alert an operator to a problem. Some assessment systems can provide a general indication of the magnitude of damage and whether the damage is spreading.

19 Claims, 18 Drawing Sheets

SYSTEM FOR ON-LINE ASSESSMENT OF THE CONDITION OF THERMAL COATING ON A TURBINE VANE

FIELD OF THE INVENTION

The invention relates in general to turbine engines and, more particularly, to turbine vanes.

BACKGROUND OF THE INVENTION

During the operation of a turbine engine, turbine vanes, among other components, are subjected to high temperature combustion gases. The vanes can be coated with a thermal insulating material or a thermal barrier coating designed to protect the vanes from such an environment. Over time, these coatings can become damaged due to wear, impact, and other factors. Failure of the coating can result in the development of unacceptably high thermal stresses, which, in turn, can result in catastrophic failure of the vane.

Currently, detection and quantification of vane coating damage is accomplished by visual inspection while the engine is off-line. Because the vanes are stationary components, many separate entries into the turbine must be made to visually inspect each of the vanes. Such a process is time consuming, laborious and expensive. Thus, there is a need for a system that can assess the condition of a thermal coating on a turbine vane during engine operation.

SUMMARY OF THE INVENTION

In one respect, aspects of the invention relate to a system for monitoring the condition of a coating on a turbine engine component. The system includes a turbine engine component, which can be, for example, an airfoil. A coating is applied over at least a portion of the turbine engine component. In one embodiment, the coating is a thermal barrier coating. One or more assessment wires can extend about at least a portion of the component such that at least a portion of each assessment wire is in contact with the coating. For instance, the one or more assessment wire can be embedded within the coating. In one embodiment, the assessment wires can include a first group of assessment wires and a second group of assessment wires. The first group of wires and the second group of wires can be angled relative to each other such that each wire from the first group of wires crosses at least one wire from the second group of wires.

The system further includes a power source electrically connected to the one or more assessment wires. An electrical current is passed along the at least one assessment wire. A measurement device is operatively associated with the at least one assessment wire so as to determine the electrical resistance across the assessment wire. Any increase in resistance measured across the assessment wires can indicate a potential disconnect in the one or more assessment wires, which can further indicate possible damage to the coating.

In one embodiment, a thermocouple can provided in contact with at least the coating. The thermocouple can measure the temperature of at least the coating. The measured temperature of the coating can be used to discount changes in the measured electrical resistance attributable to a change in temperature.

In another respect, aspects of the invention relate to a system for monitoring the condition of a coating on an airfoil. The airfoil has a radially inner end and a radially outer end. The airfoil defines an outer peripheral surface. A thermal coating substantially covers the outer peripheral surface of the airfoil. A plurality of assessment wires extend about at least a portion of the airfoil. For example, the plurality of wires can extend from near one radial end of the airfoil to near the opposite radial end of the airfoil. Further, the plurality of wires can extend substantially about the leading edge of the airfoil. In one embodiment, the plurality of wires can be substantially equally spaced.

At least a portion of each assessment wire is in contact with the thermal coating. In one embodiment, the plurality of assessment wires can be embedded in the thermal coating. Alternatively, the plurality of assessment wires can be disposed beneath the thermal coating, or they can be disposed over the thermal coating.

At least some of the plurality of wires can be electrically insulated from the rest of the plurality of wires. In one embodiment, the plurality of wires can include at least a first group of wires and a second group of wires. The first group of wires and the second group of wires can be angled relative to each other such that each wire from the first group of wires crosses at least one wire from the second group of wires. For at least some of these crossing points, the first and second groups of wires can be electrically connected.

A power source is electrically connected with the plurality of assessment wires. An electrical current is passed along the plurality of assessment wires. In one embodiment, a first wire and a second wire can be operatively associated with the power source. Each of the plurality of assessment wires can be electrically connected at one end to the first wire and at the other end to the second wire. The first wire can deliver the electrical current to each of the plurality of assessment wires, and the second wire can receive current from each of the assessment wires.

A measurement device is operatively associated with the plurality of assessment wires so as to determine the electrical resistance across the assessment wires. Thus, increases in resistance measured across the assessment wires can provide information as to the size and growth of possible damage to the thermal coating.

In yet another respect, aspects of the invention relate to a method of evaluating the condition of a coating on a turbine engine during on-line operation of the engine. According to the method, a turbine engine is provided. The turbine engine has a component that is at least partially covered with a thermal coating. One or more assessment wires extend about at least a portion of the component such that at least a portion of each assessment wire is in contact with the coating.

An electrical current is supplied to the at least one assessment wire, and the resistance across the one or more assessment wires is determined. The supplying and measuring steps can be performed during engine operation. The resistance can be monitored for changes. An increase in the resistance across the one or more assessment wires can provide a general assessment of the condition of the thermal coating. In one embodiment, the step of measuring can be conducted on a substantially continuous basis.

DETAILED DESCRIPTION OF EMBODIMENTS OF THE INVENTION

Figure 1:
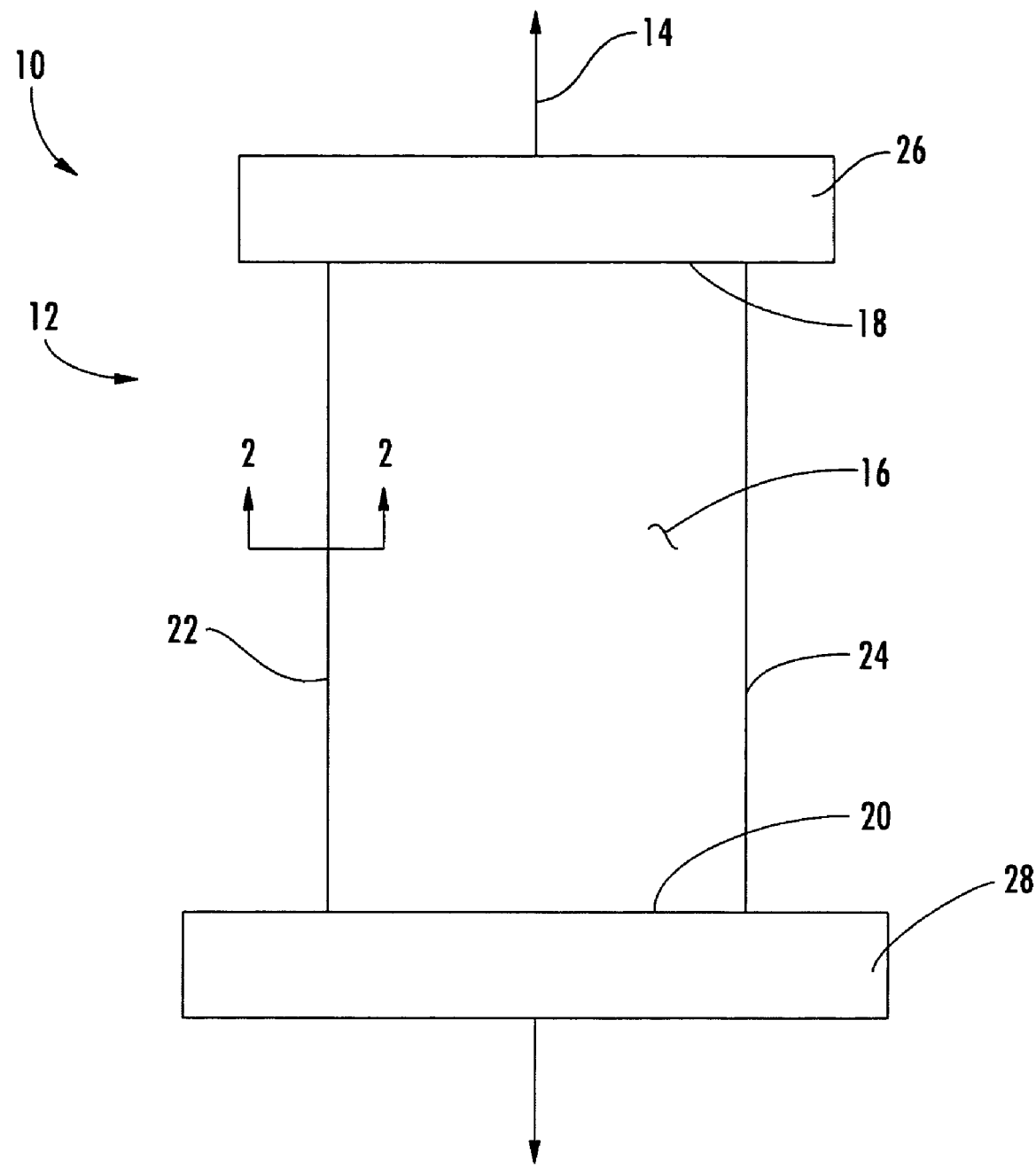
FIG. 1 is a side elevational view of a turbine vane.

Embodiments of the present invention address the inadequacies of prior vane coating inspection methods. Embodiments of the invention will be explained in the context of one possible system, but the detailed description is intended only as exemplary. Embodiments of the invention are shown in FIGS. 1–16, but the present invention is not limited to the illustrated structure or application.

A turbine vane 10 can include an elongated airfoil 12 defining a longitudinal axis 14. The airfoil 12 can have an outer peripheral surface 16 as well as a radial inner end 18 and a radial outer end 20. The terms "radial inner" and "radial outer," as used herein, are intended to refer to the positions of the ends of the airfoil 12 relative to the turbine when the vane 10 is installed in its operational position. The airfoil 12 can have a leading edge 22 and a trailing edge 24. The airfoil 12 can be made of any of a number of materials including, for example, metal or ceramic matrix composite.

At least one of the radial ends of the airfoil 12 can be attached to a shroud. For example, the radial inner end 18 of the airfoil 12 can be attached to an inner shroud 26. The inner shroud 26 can be adapted to host a seal housing or other structure. In addition, the radial outer end 20 of the airfoil 12 can be attached to an outer shroud 28. The outer shroud 28 can be adapted to facilitate attachment to a surrounding stationary support structure, such as a vane carrier. The inner and outer shrouds 26, 28 can enclose a single airfoil 12 or multiple circumferentially spaced airfoils (not shown).

Figure 2:
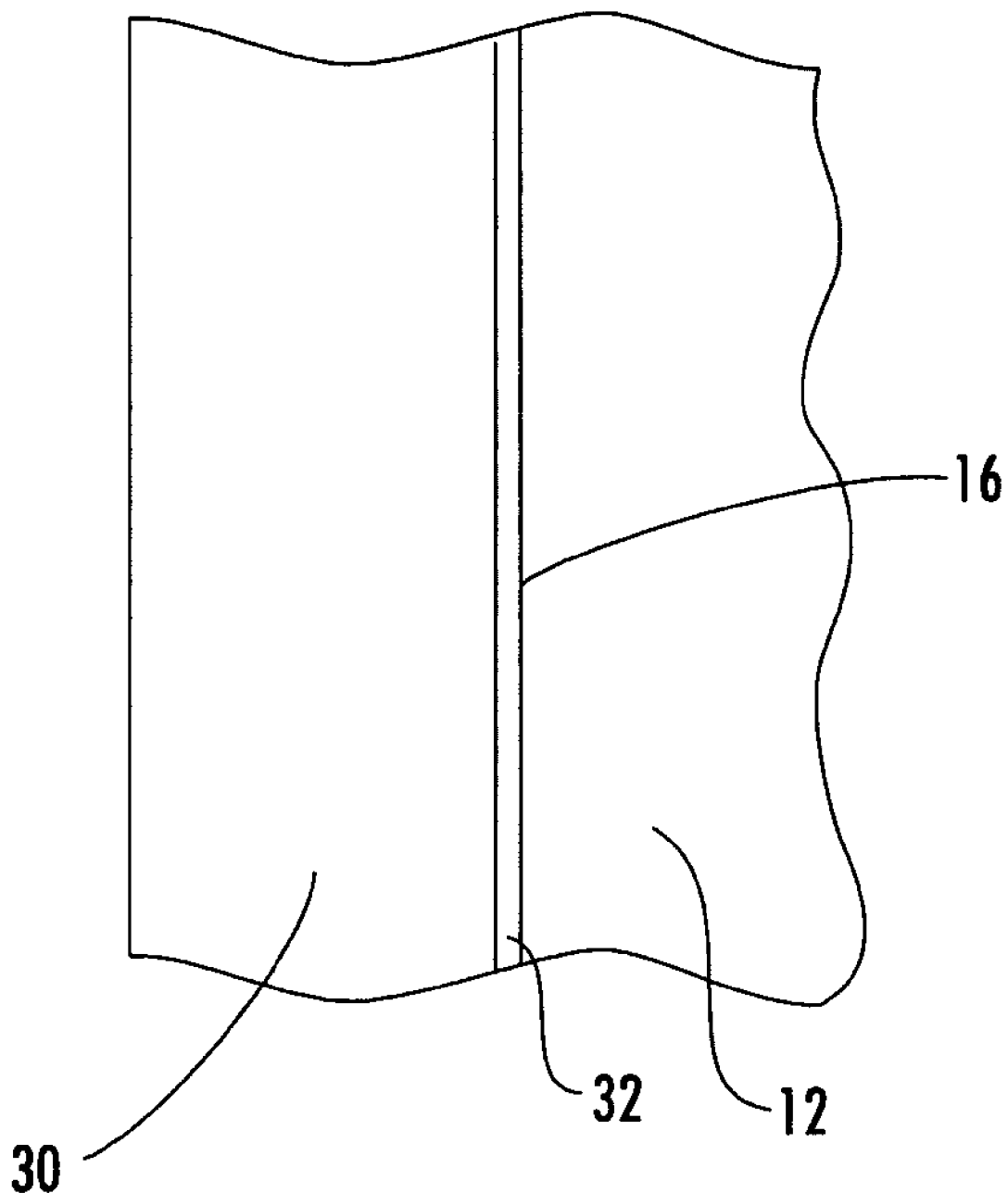
FIG. 2 is a cross-sectional view of a portion of a turbine vane, showing a primer layer and a thermal coating over the outer peripheral surface of the airfoil portion of the vane.

At least a portion of the outer peripheral surface 16 of the airfoil 12 can be coated with a thermal insulating material or a thermal barrier coating 30 (referred to herein as "thermal coating"). Such coatings are known, and examples of such coatings are disclosed in U.S. Pat. Nos. 6,676,783; 6,641,907; 6,287,511; and 6,013,592, which are incorporated herein by reference. The thermal coating 30 can be applied in a single layer or in multiple layers. The thermal coating 30 can be directly applied to the outer peripheral surface 16 of the airfoil 12. In some cases, a primer coating 32 can be applied to the outer peripheral surface 16 of the airfoil 12 before application of the thermal coating 30, as shown in FIG. 2. While particularly suited for thermal coatings, embodiments of the invention can be applied to any coating applied over at least a portion of the outer peripheral surface 16 of the airfoil 12.

According to aspects of the invention, one or more conductors or conductive assessment wires 34 can be provided along the airfoil portion 12 of the vane 10. It will be understood that the term "wires," as used herein, encompasses a single wire in addition to at least two wires. In addition, the term "assessment" is associated with the wires 34 for convenience so as to distinguish the wires 34 from other wires in the system. It is not intended for the term "assessment" to be limiting.

A variety of assessment wires 34 are encompassed within aspects of the invention. The assessment wires 34 can be any size, but it is preferred if the assessment wires 34 are as small as possible. In one embodiment, the cross-sectional dimensions of an assessment wire 34 can be about 0.008 inches by about 0.001 inches. The assessment wires 34 can have any cross-sectional shape. For instance, the assessment wires 34 can be circular, semi-circular, square or rectangular, just to name a few possibilities.

The assessment wires 34 can be made of any of a variety of materials including, for example, copper, silver and alloys. In some instances, the assessment wires 34 can be made of a material that can withstand the high temperature environment of the turbine section of the engine. The assessment wires 34 can be provided as bare wires, or they can be provided with an outer protective or insulating covering.

The assessment wires 34 can be provided about at least a portion of the airfoil 12 in several ways. For instance, the assessment wires 34 can cover substantially the entire airfoil portion 12 of the vane 10. Alternatively, the assessment wires 34 can be provided in localized areas, such as in areas of high thermal loads or in areas of expected failures. In one embodiment, the assessment wires 34 can be provided about the leading edge portion 22 of the airfoil 12.

Figure 3A:
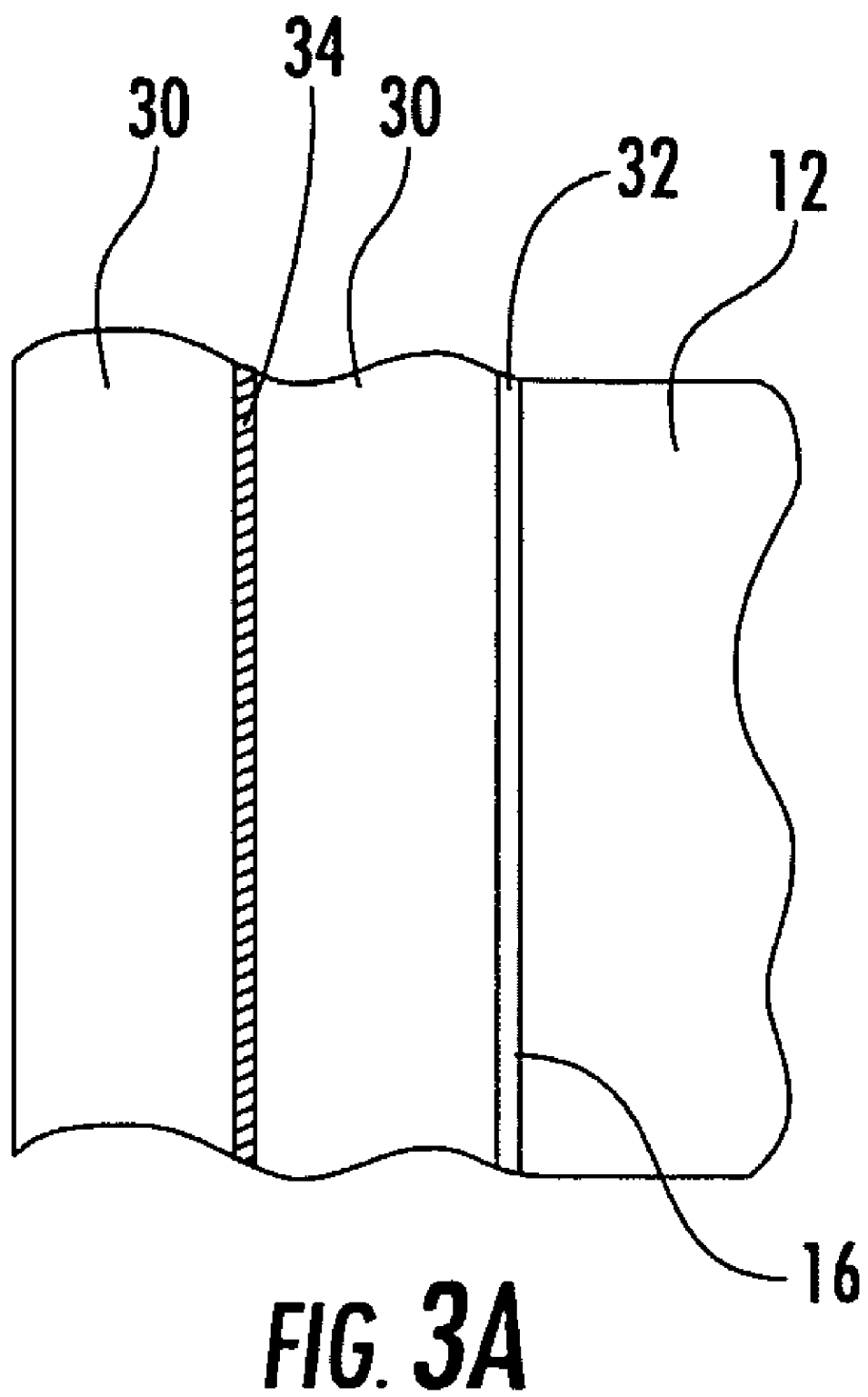
FIG. 3A is a cross-sectional view of a portion of a turbine vane according to aspects of the invention, showing an assessment wire disposed within the thermal coating.
Figure 3B:
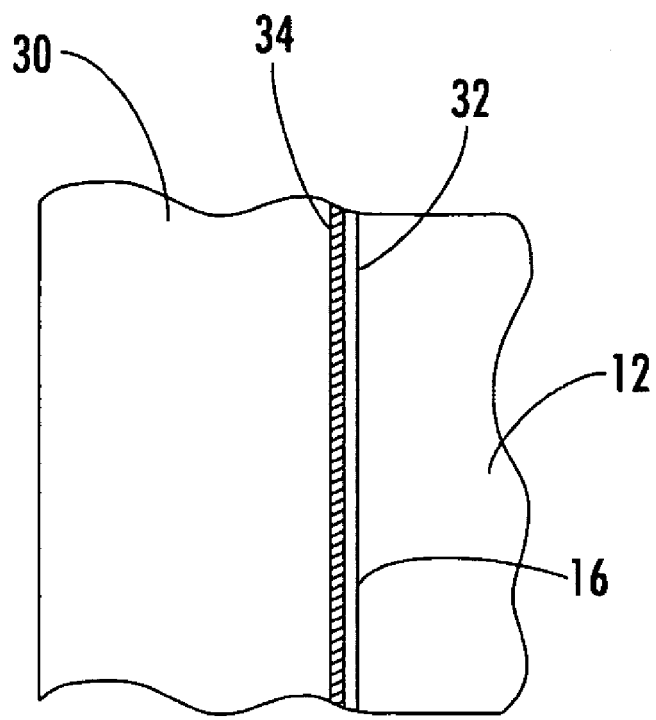
FIG. 3B is a cross-sectional view of a portion of a turbine vane according to aspects of the invention, showing an assessment wire disposed between the thermal coating and the primer layer.
Figure 3C:
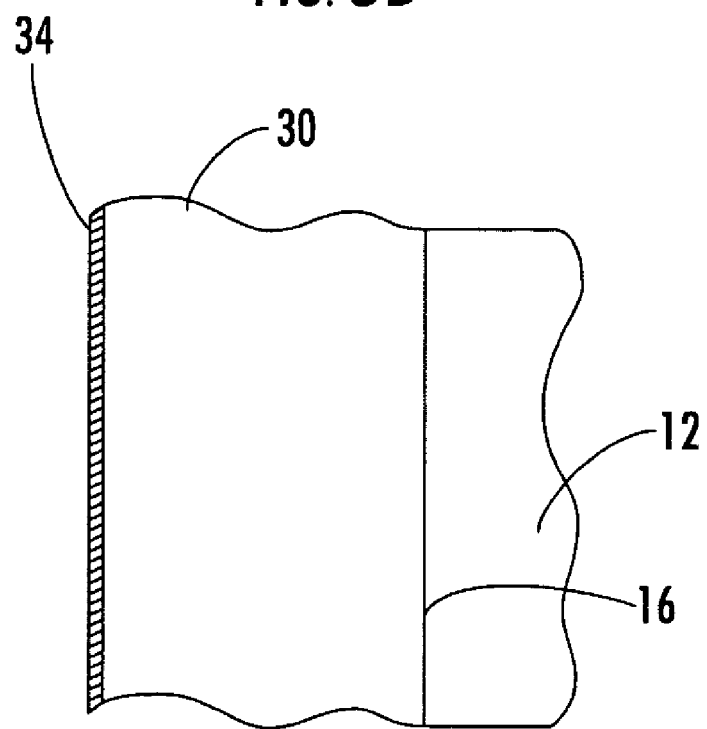
FIG. 3C is a cross-sectional view of a portion of a turbine vane according to aspects of the invention, showing an assessment wire disposed over the thermal coating.

The assessment wires 34 can be positioned relative to the thermal coating 30 in several ways. Preferably, the assessment wires 34 are embedded within the thermal coating 30, as shown in FIG. 3A. Thus, when applying the thermal coating 30, the assessment wires 34 can be laid down after a layer of the thermal coating 30 has been applied but before a subsequent layer of the thermal coating 30 is applied. Alternatively, the assessment wires 34 can be positioned beneath the thermal coating 30. In such case, it is preferred if the assessment wires 34 and the outer peripheral surface 16 of the airfoil 12 are electrically insulated by, for example, an insulating film or a primer coat 32 applied to the outer peripheral surface 16 of the airfoil 12, as shown in FIG. 3B. Yet another possibility is for the assessment wires 34 to be provided over the thermal coating 30, as shown in FIG. 3C. In such case, the assessment wires 34 can be positioned so as not to interfere with aerodynamic performance of the vane 10. In any of these arrangements, the assessment wires 34 can be individually insulated from the other assessment wires 34 by the thermal coating 30 or by a coating provided on an individual assessment wire 34.

Figure 4:
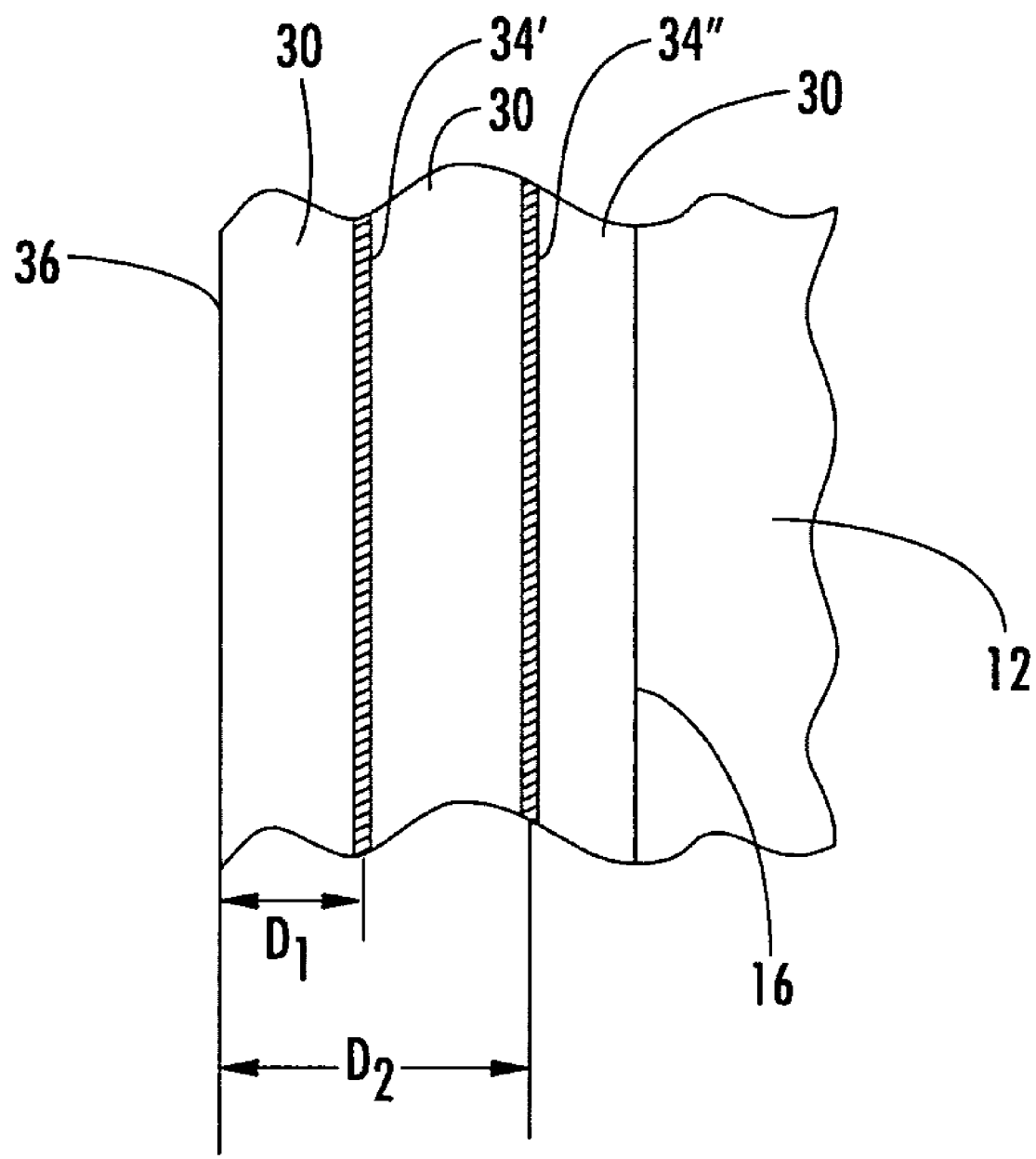
FIG. 4 is a cross-sectional view of a portion of a turbine vane according to aspects of the invention, showing two assessment wires disposed at different depths from the outermost surface of the thermal coating.

The assessment wires 34 can be provided at multiple levels. One possible multi-level assessment wire arrangement is shown in FIG. 4. A first layer of assessment wires 34' can be provided within the thermal coating 30 at a first depth D1 relative to the outer surface 36 of the thermal coating 30, and a second layer of assessment wires 34" can be provided within the thermal coating 30 at a second depth D2. The various layers of assessment wire 34', 34" can be insulated from each other by one or more layers of the thermal coating 30.

Figure 5:
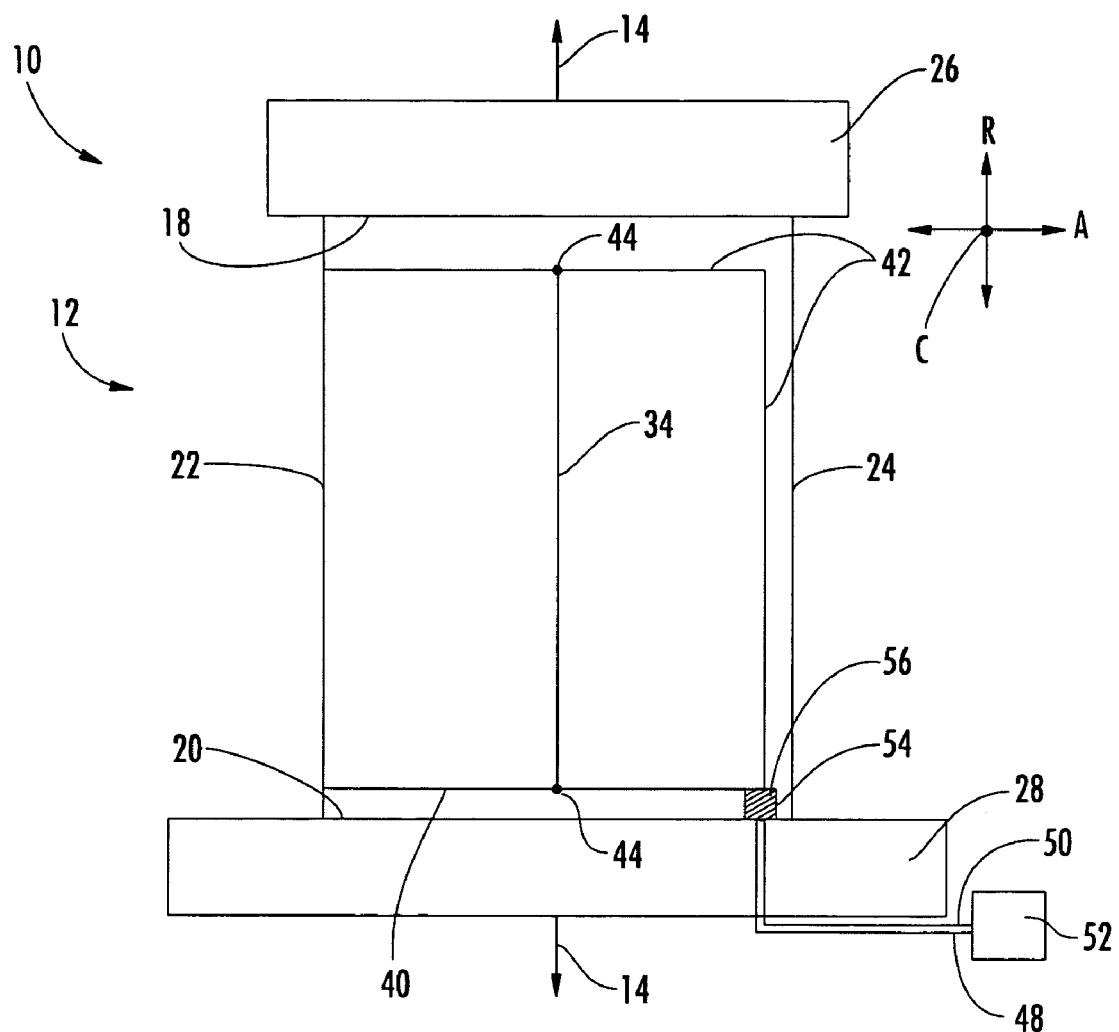
FIG. 5 is a side elevational view of a turbine vane according to aspects of the invention, showing a first assessment wire configuration.
Figure 6:
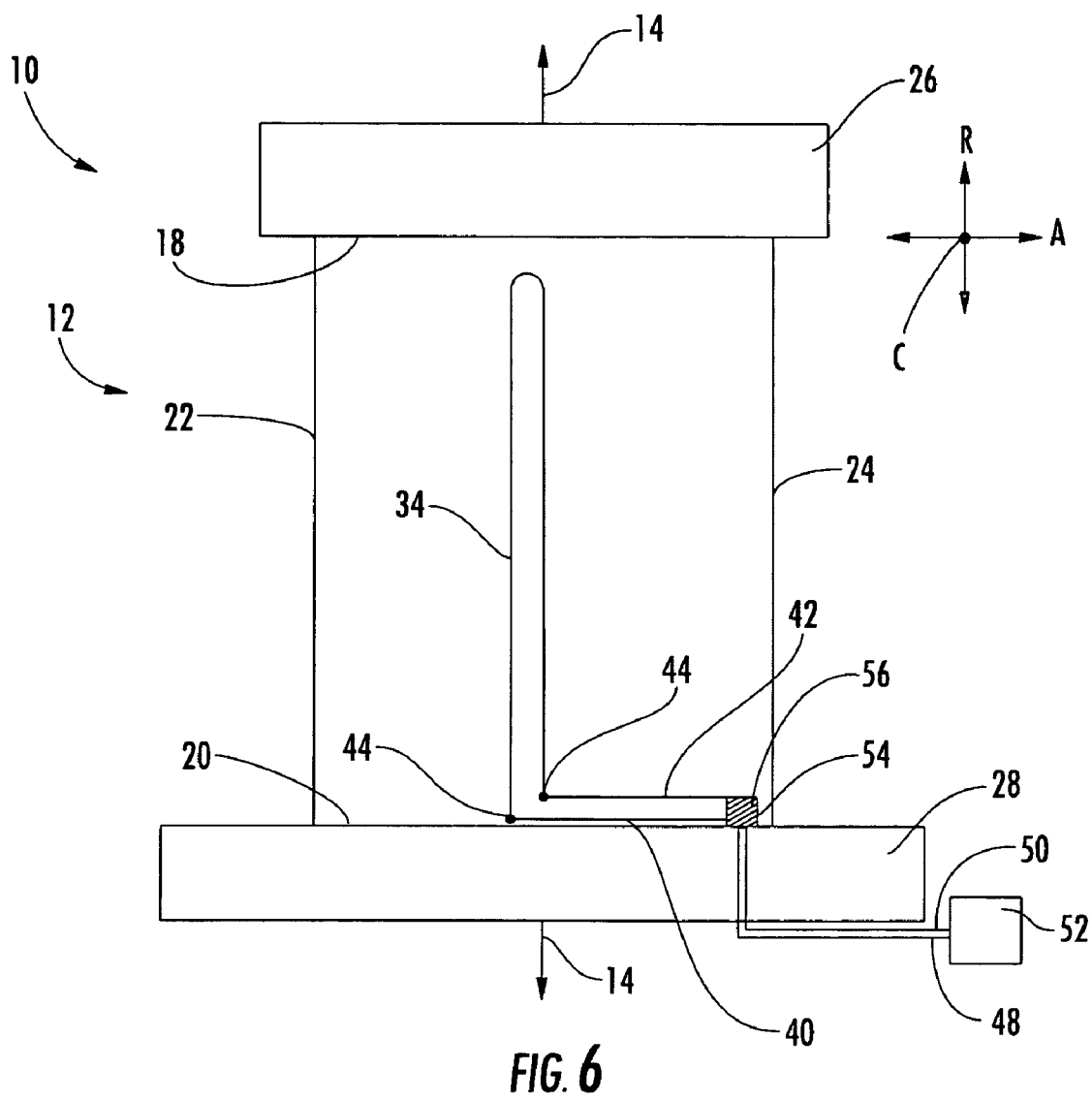
FIG. 6 is a side elevational view of a turbine vane according to aspects of the invention, showing a second assessment wire configuration.
Figure 7:
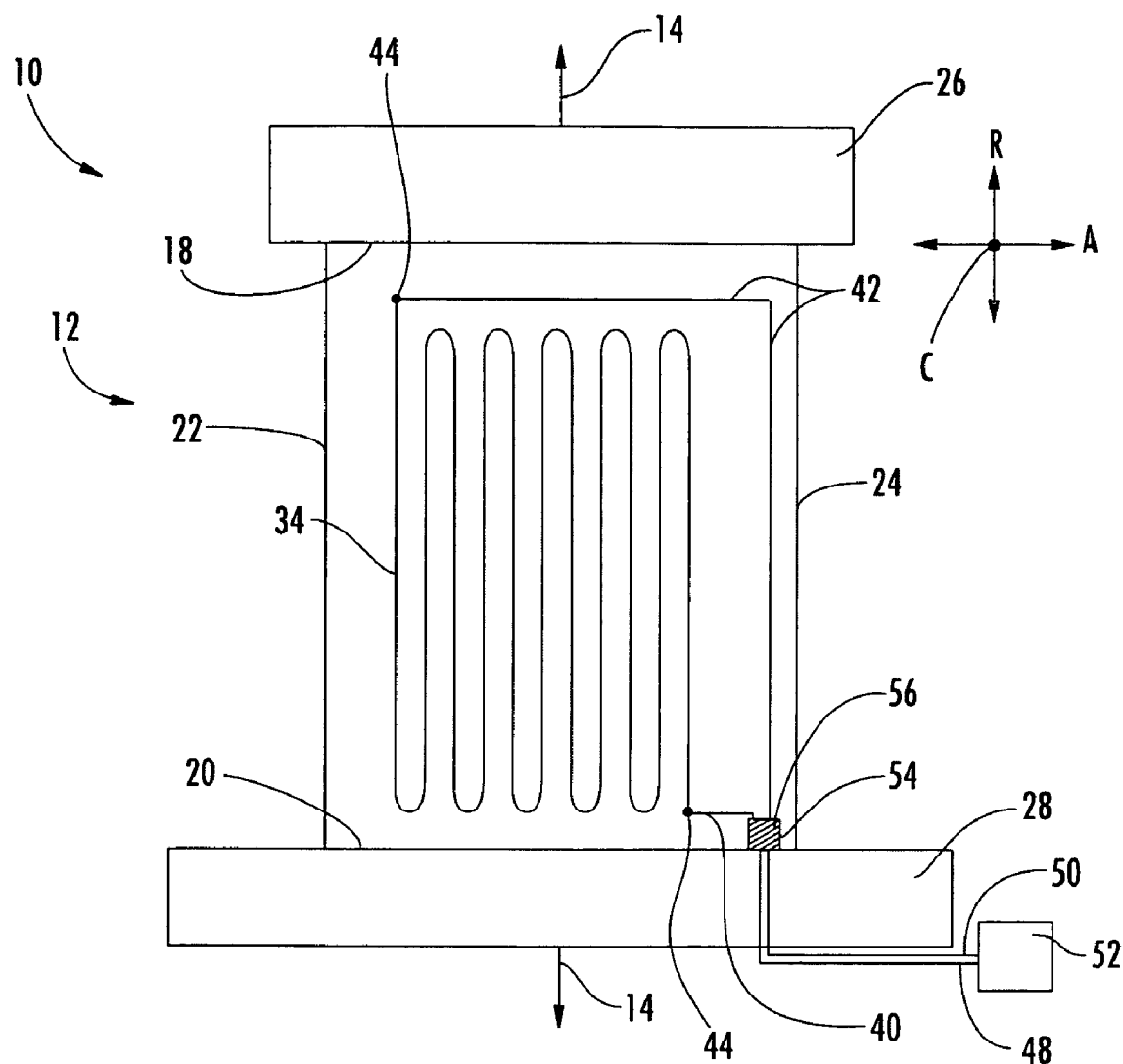
FIG. 7 is a side elevational view of a turbine vane according to aspects of the invention, showing a third assessment wire configuration.

Again, there can be any number of assessment wires 34 extending along the airfoil 12. In one embodiment, there can be a single assessment wire 34; in other embodiments, there can be more than one assessment wire 34. In either case, the assessment wires 34 can be arranged in a variety of ways. In one embodiment, a single assessment wire 34 can extend along the airfoil 12 generally in the radial direction R between the radial inner and outer ends 18, 20, as shown in FIG. 5. However, the assessment wire 34 can extend in any of a number of directions along the airfoil 12, including the axial direction A and the circumferential direction C. In one embodiment, the assessment wire 34 can be formed in a generally U-shaped loop, as shown in FIG. 6. In another embodiment, the assessment wire 34 can be formed as a series of generally U-shaped loops, as shown in FIG. 7. The foregoing arrangements are merely examples, and various configurations for a single assessment wire system will readily be appreciated.

Figure 8:
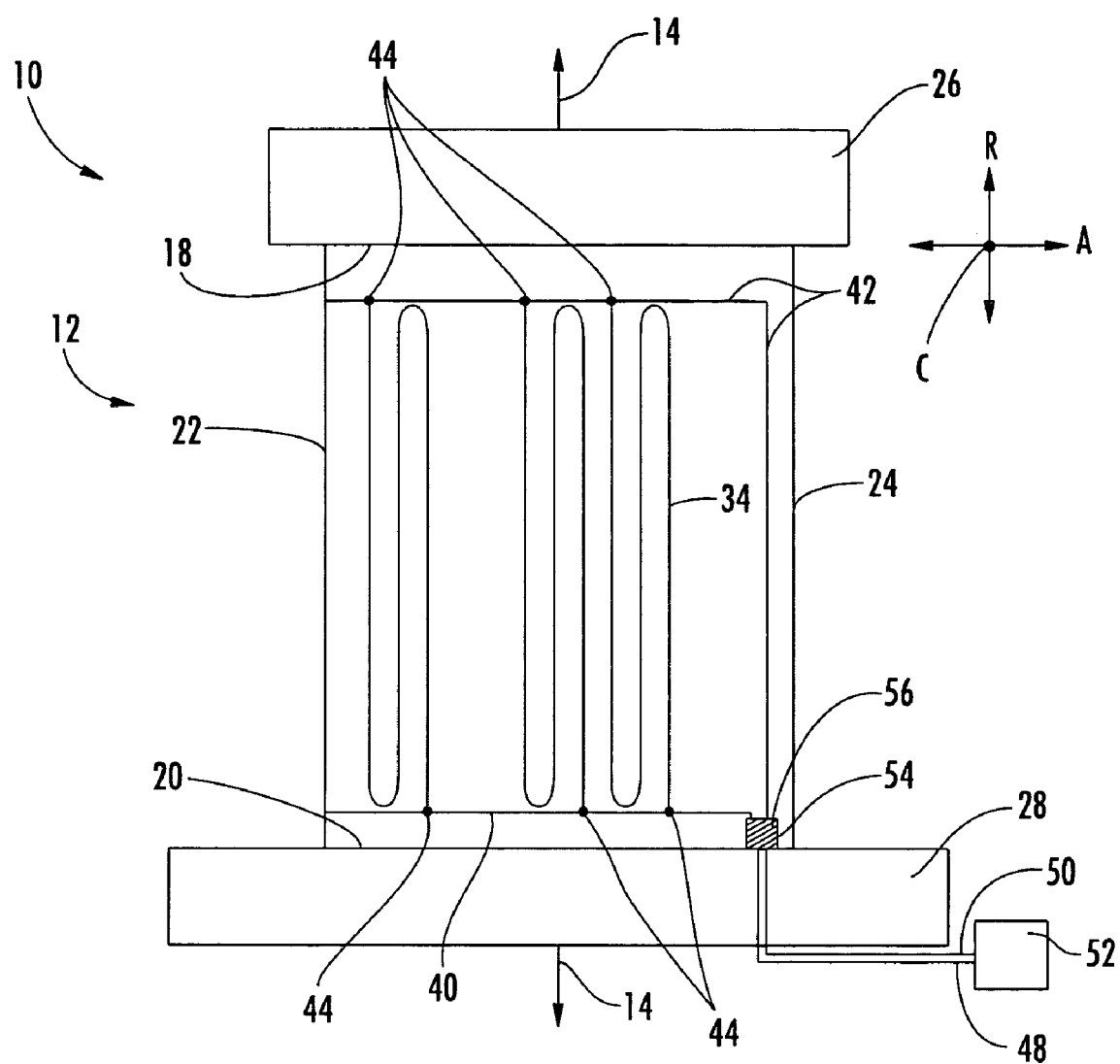
FIG. 8 is a side elevational view of a turbine vane according to aspects of the invention, showing a first configuration of multiple assessment wires.
Figure 9:
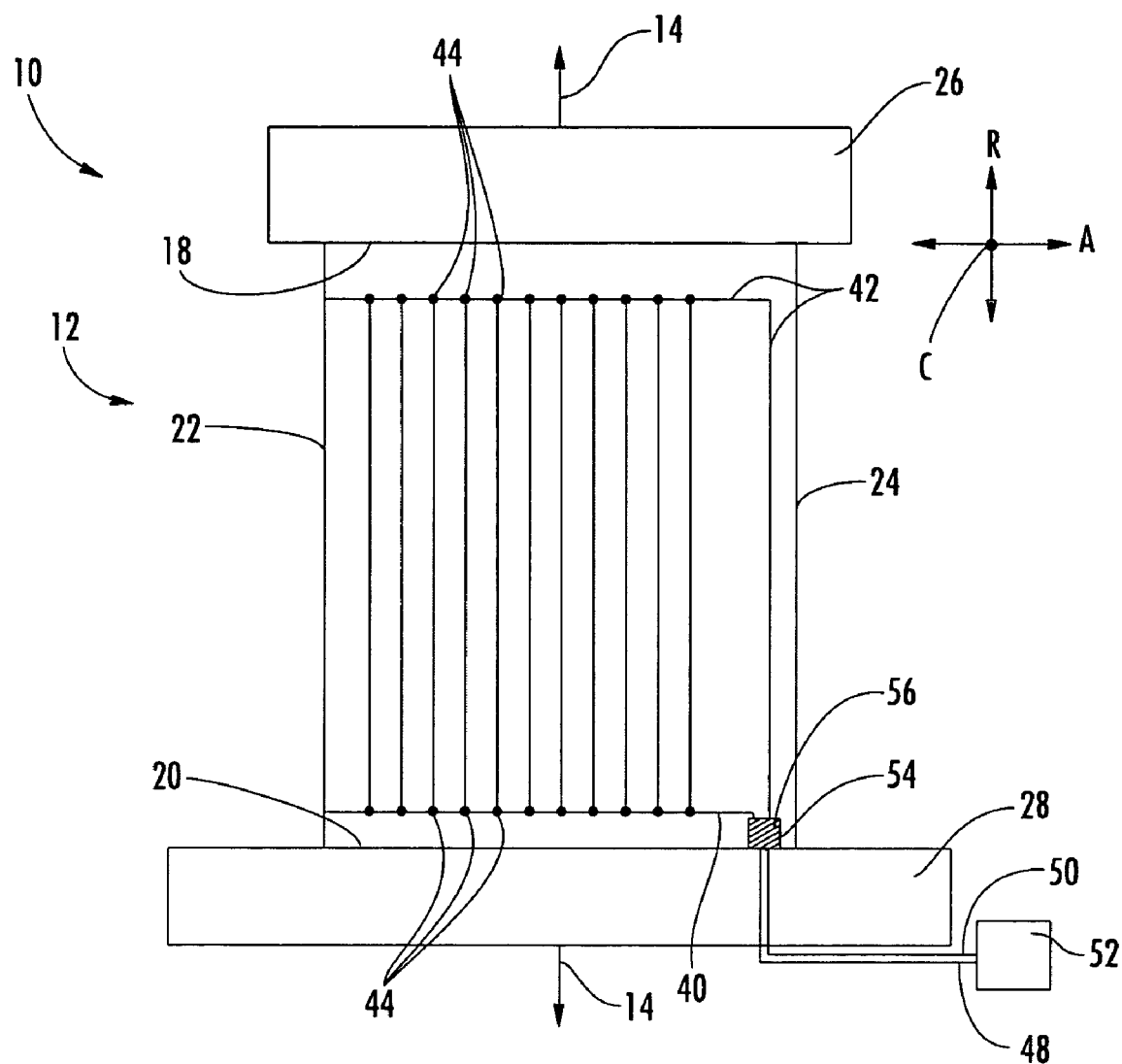
FIG. 9 is a side elevational view of a turbine vane according to aspects of the invention, showing a second configuration of multiple assessment wires.
Figure 10:
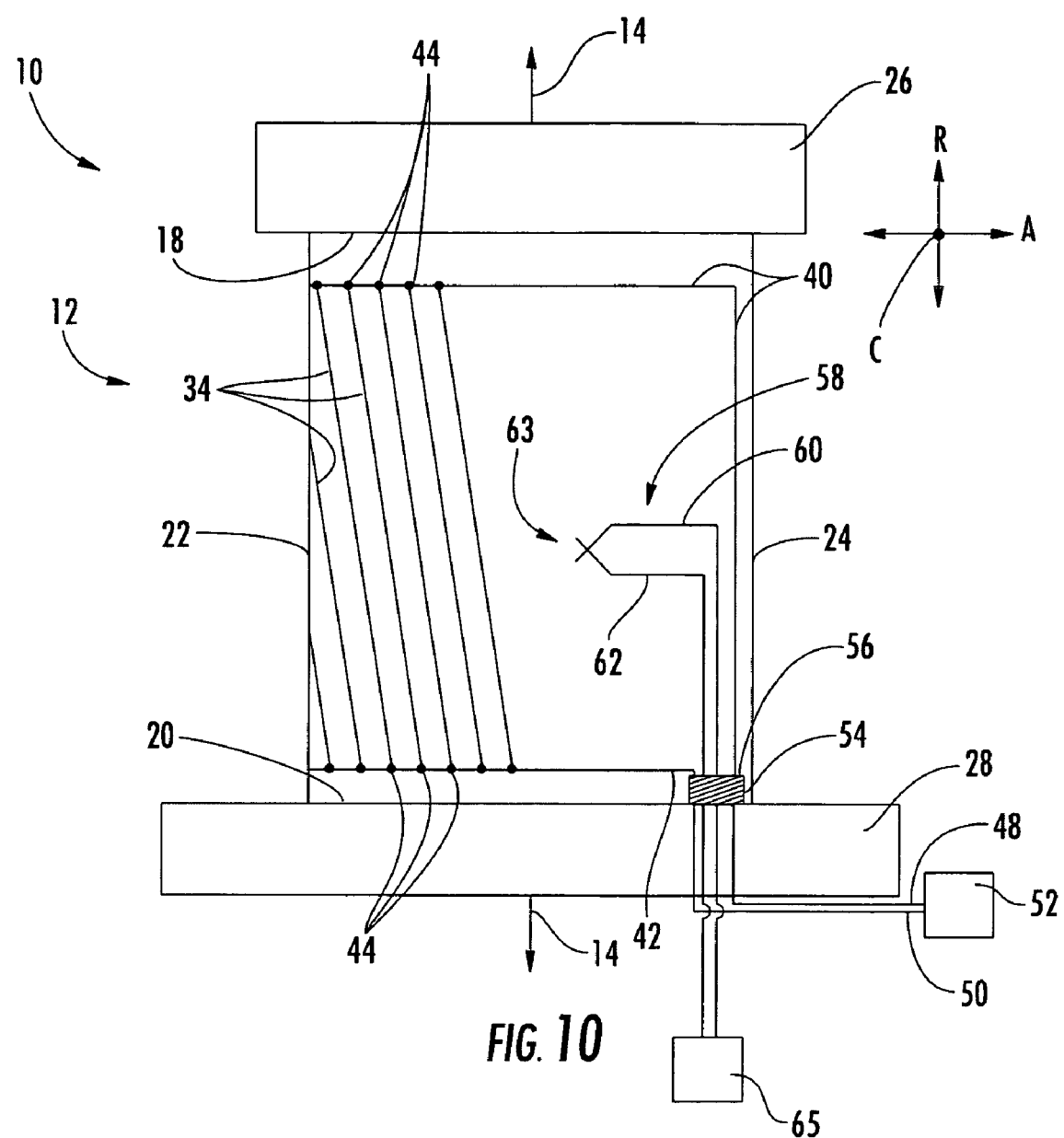
FIG. 10 is a side elevational view of a turbine vane according to aspects of the invention, showing a third configuration of multiple assessment wires.
Figure 11:
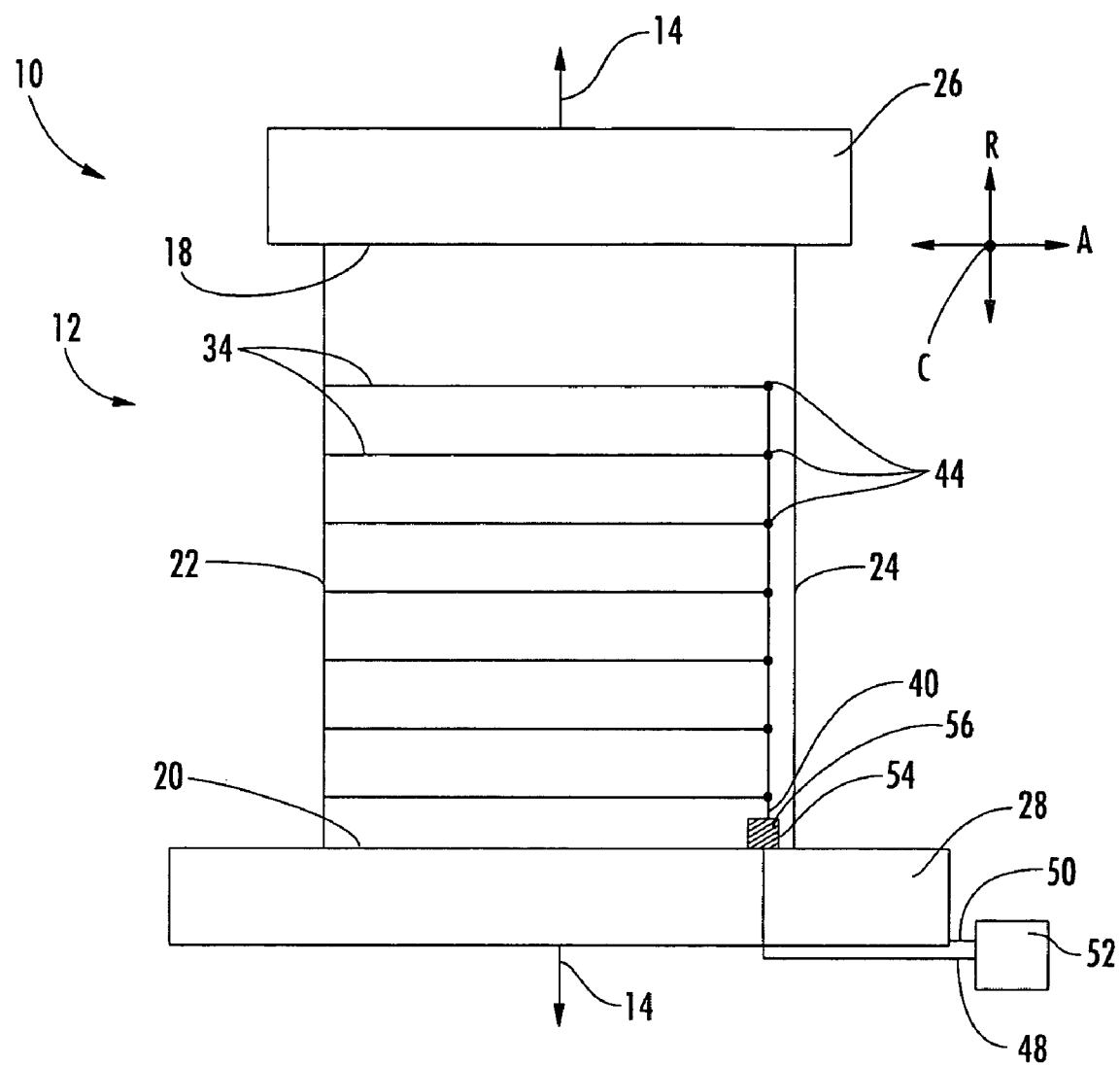
FIG. 11 is a side elevational view of a turbine vane according to aspects of the invention, showing a fourth configuration of multiple assessment wires.

Similarly, there are numerous ways in which a plurality of assessment wires 34 can be arranged on the airfoil 12. For instance, a plurality of individual assessment wires 34 can be used to form U-shaped loops, as shown in FIG. 8. In another embodiment, the plurality of assessment wires 34 can extend along the airfoil 12 in substantially the radial direction R, as shown in FIG. 9. The term "substantially" refers to true radial as well as deviations therefrom, such as from surface contours of the airfoil 12. In another embodiment, the assessment wires 34 can be angled relative to the longitudinal axis 14 of the airfoil 12. As shown in FIG. 10, the assessment wires 34 can all extend at substantially the same angle relative to the longitudinal axis 14 of the airfoil 12. A further possible arrangement is for the assessment wires 34 to span circumferentially and/or axially (relative to the turbine) designated by C, A, respectively, about the airfoil 12, as shown in FIG. 11. In other words, the assessment wires can be at substantially 90 degrees relative to the longitudinal axis 14 of the airfoil 12. While appearing to be substantially straight in the figures, the assessment wires 34 follow the contour of the outer peripheral surface 16 of the airfoil 12. In addition, the assessment wires 34 can routed as needed to avoid features provided in the airfoil 12, such as cooling holes.

Figure 12:
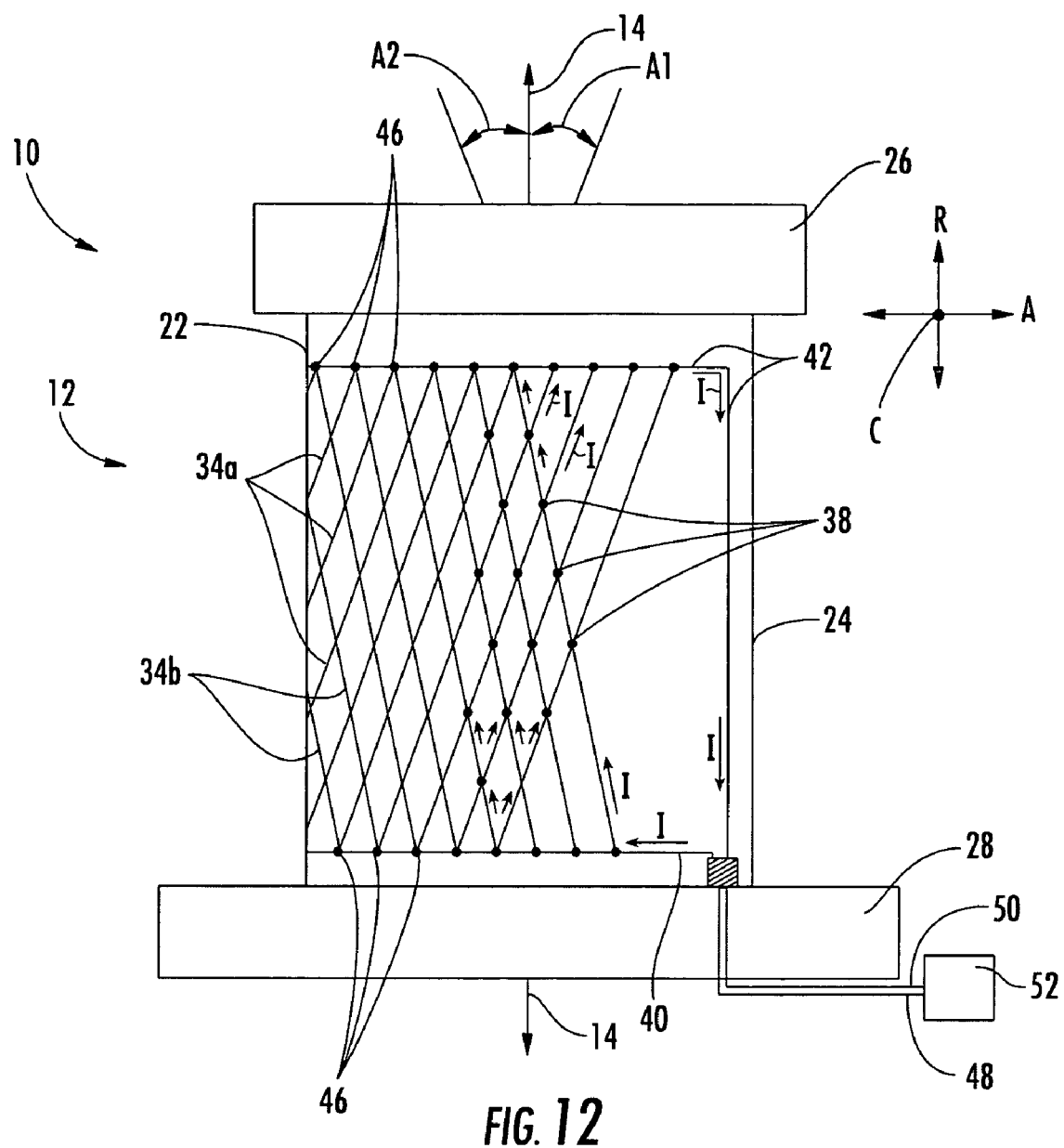
FIG. 12 is a side elevational view of a turbine vane according to aspects of the invention, showing a fifth configuration of multiple assessment wires.
Figure 13:
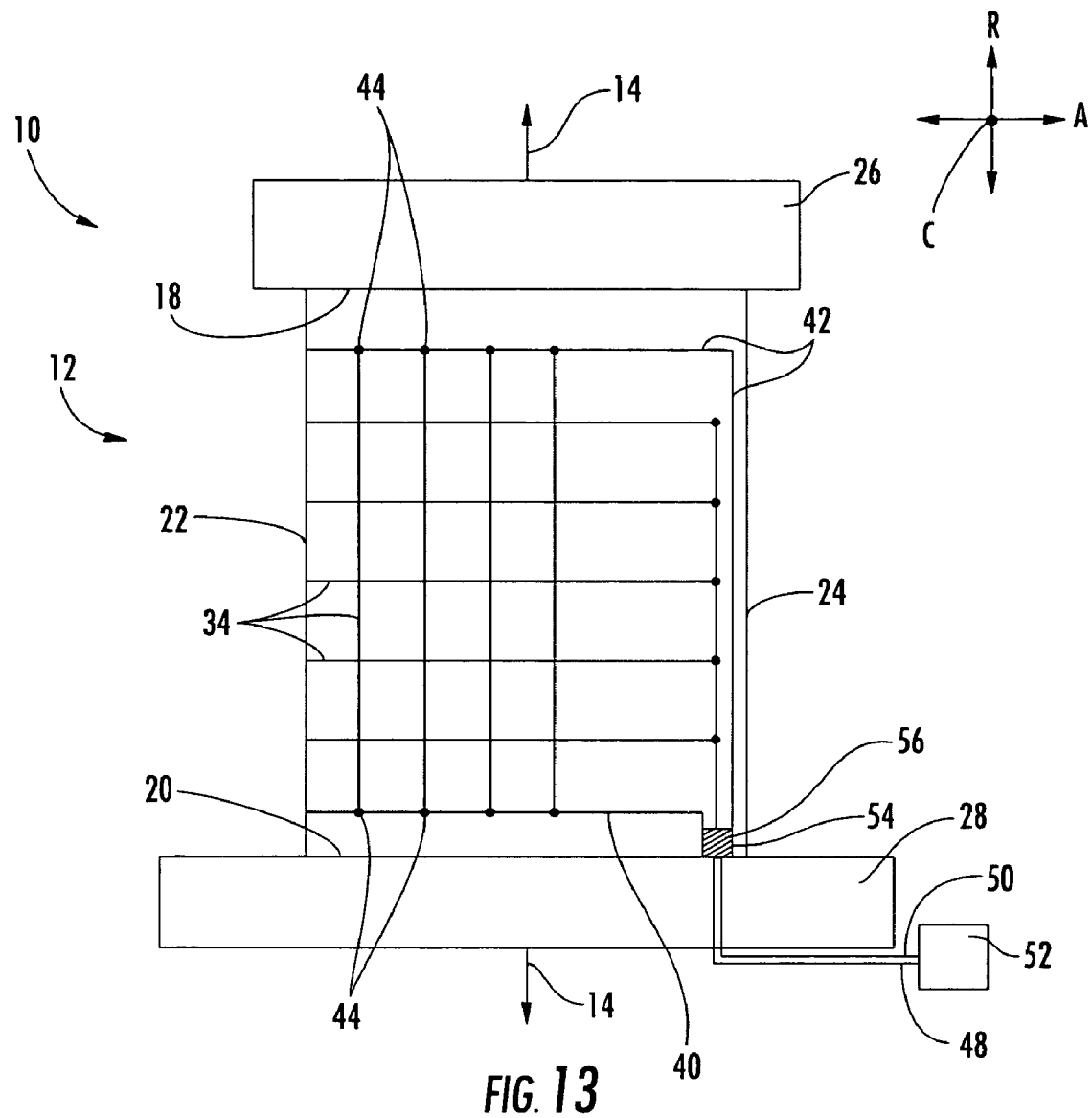
FIG. 13 is a side elevational view of a turbine vane according to aspects of the invention, showing a sixth configuration of multiple assessment wires.

The assessment wires 34 can extend at more than one angle relative to the longitudinal axis 14 of the airfoil 12. That is, the assessment wires 34 can be angled relative to each other such that at least some of the assessment wires 34 cross. The assessment wires 34 can be angled at almost any orientation relative to each other. In one embodiment, shown in FIG. 12, a first group of assessment wires 34a can extend at a first angle A1 relative to the longitudinal axis 14 of the airfoil 12, and a second group of assessment wires 34b can extend at a second angle A2 relative to the longitudinal axis 14 of the airfoil 12. The first and second angles A1, A2 can be unequal such that the first group of assessment wires 34a cross the second group of assessment wires 34b so as to form a net-like arrangement. In one embodiment, the first group of assessment wires 34a can extend substantially parallel to the longitudinal axis 14 of the airfoil 12, and the second group of assessment wires 34b can extend substantially perpendicular to the longitudinal axis 14 of the airfoil 12, as shown in FIG. 13. The various possible arrangement between the first group of assessment wires 34a and the second group of assessment wires 34b will readily be appreciated. It will be understood that embodiments of a multi-assessment wire system according to aspects the invention are not limited to only two groups of assessment wires. It will readily be appreciated that additional groups of assessment wires can be provided.

In the case of systems having more than one assessment wire 34, each assessment wire 34 can be electrically insulated from the other assessment wires 34. However, in some instances, at least one of the assessment wires 34 can be electrically connected to at least one other assessment wire 34. For example, as shown in FIG. 12, electrical connections 38 can be made at each point where the assessment wires 34 overlap. As will be explained later, electrically connecting the assessment wires 34 can affect the sensitivity of the response of system according to aspects of the invention.

Whether a single assessment wire or multiple assessment wires 34 are used, a first wire 40 and a second wire 42 can be used to supply and route electrical current through the wires. Referring to FIG. 12, the first wire 40 can be provided at or near the radial outer end 18 of the airfoil 12, and the second wire 42 can be provided at or near the radial inner end 20 of the airfoil 12. In such case, the first and second wires 40, 42 can run substantially perpendicular to the longitudinal axis 14 of the airfoil 12. Such an arrangement is provided merely as an example, and it will be understood that other locations for the first and second wires 40, 42 are possible. For instance, the first wire 40 can be provided at or near the radial inner end 18 of the airfoil 12, and the second wire 42 can be provided at or near the radial outer end 20 of the airfoil 12, as shown in FIG. 10. Alternatively, the first and second wires 40, 42 can both be located near one end of the airfoil 12, such as near the radial inner end 18 of the airfoil 12, as shown in FIG. 6. Yet another possibility is for the first and second wires 40, 42 to extend substantially parallel to the longitudinal axis 14 of the airfoil 12. In such case, the first and second wires 40, 42 can be provided near the trailing edge 24 of the airfoil 12, as shown in FIG. 11 (only the first wire 40 is shown, and the second wire 42 can be on the opposite side of the airfoil 12). The first and second wires 40, 42 may or may not be substantially parallel to each other. Each of the assessment wires 34 can be electrically connected 44 at one end to the first wire 40 and at the opposite end to the second wire 42. In one embodiment, at least two assessment wires 34 share a common electrical connection 46 with the first and second wires 40, 42, as shown in FIG. 12.

The assessment wires 34 and the first and second wires 40, 42 can be included on the vane 10 in a number of ways. Preferably, these wires 34, 40, 42 are vapor deposited on the substrate, which, as noted above, can be the airfoil 12, a primer coat 32 and/or the thermal coating 30. Vapor deposition of the wires 34, 40, 42 can be computer controlled, allowing for the benefits of rapid, accurate and repeatable formation of the wires 34, 40, 42. Alternatively, at least some of the wires 34, 40, 42 can be conventional conductor wires. In such case, the wires 34, 40, 42 can be provided on a spool and laid down by hand.

The first and the second wires 40, 42 can be electrically connected to respective first and second source wires 48, 50. At their other ends, the source wires 48, 50 can be electrically connected, directly or indirectly, to any suitable source of electrical current 52. In one embodiment, the source wires 48, 50 can extend outside of the turbine and connect to an external power source 52. The source wires 48, 50 can be conventional wires. The junction between the source wires 48, 50 and the first and second wires 40, 42 can occur within the turbine section of the engine. For instance, the first and second wires 40, 42 can be brought to substantially adjacent points on the turbine vane 10 for connection to the first and second source wires 48, 50. In such case, it is preferred if the junction 54 is as far from the turbine gas path as possible. In one embodiment, the junction 54 can be on or near one of the outer shroud 28. The junction 54 and possibly at least a portion of the source wires 48, 50 and/or first and second wires 40, 42 can be provided within a housing 56, such as a tube, to protect them from the environment of the turbine. In one embodiment, the source wires 48, 50 can be routed through the inside of the airfoil and/or shrouds 26, 28, such as through an internal cooling channel.

The source wires 48, 50 can be electrically connected to the first and second wires 40, 42 in several ways. For instance, the source wires 48, 50 and the first and second wires 40, 42 can be connected by conductive paint. In one embodiment, the conductive paint can include silver in suspension. Other manners of achieving electrical connection between the source wires 48, 50 and the first and second wires 40, 42 include spot welding or laser welding, just to name a few possibilities.

In one embodiment, a thermocouple 58 can be provided on the airfoil 12, as shown in FIG. 10. The thermocouple 58 can be provided above, within or under the thermal coating 30, as discussed above in connection with the assessment wires 34. The thermocouple can include two thermocouple wires 60, 62 made of different materials. The wires can make a connection 63. Preferably, the connection is located in a radially central region of the airfoil 12. The thermocouple 58 can be disposed in a radially central location of the airfoil 12. A pair of thermocouple wires 60, 62 can extend from the thermocouple 58. The thermocouple wires 60, 62 can be electrically connected, directly or indirectly, with a detection circuit 65, which can convert the measured thermocouple junction voltage into temperature.

A vane 10 according to embodiments of the invention can be provided in the turbine section in a variety of ways. For instance, in a row of turbine vanes, at least one of the vanes can be configured according to embodiments of the invention. In one embodiment, each vane in the row can be configured according to aspects of the invention. In another embodiment, only those vanes that are more susceptible to damage, based on experience or otherwise, can be configured according to aspects of the invention. In some rows, there may not be any need for a vane with an assessment system according to aspects of the invention. Generally, the upstream rows of vanes in a turbine are ideal for the assessment system according to aspects of the invention, particularly the first row of vanes, because these vanes experience the greatest thermal loads.

One manner of using a vane assembly 10 according to embodiments of the invention will now be described. It should be noted that the following method is provided as an example. It is not intended for embodiments of the invention to be limited to the following steps or to performance in the order described.

An electrical current I can be passed along the assessment wires 34. The current I can be supplied from any suitable electrical source, which may or may not be external to the engine. The current I can be supplied to one of the first and second wires 40, 42. The current I can flow through the assessment wires 34 and to the other of the first and second wires 40, 42. In one embodiment, the current I can flow from the first wire 40 at or near the radial outer end 20 of the airfoil 12 to the second wire 42 at or near the radial inner end 18 of the airfoil 12.

According to aspects of the invention, the electrical resistance of the assessment wires 34 can be measured during on-line operation of the engine. The measurement can be made on a continuous basis or according to a regular or irregular interval. A measuring device 64 can be used to measure resistance. The measuring device 64 can be, for example, a voltmeter, multi-meter or an ohmmeter. It should be noted that aspects of the invention include direct and indirect measurements of resistance. One manner of indirectly measuring resistance is to measure voltage across the assessment wires 34 as a substantially constant current is passed through the assessment wires 34. Using Ohm's Law, the resistance can be calculated from the measured voltage and for a known input current I.

Figure 16A:
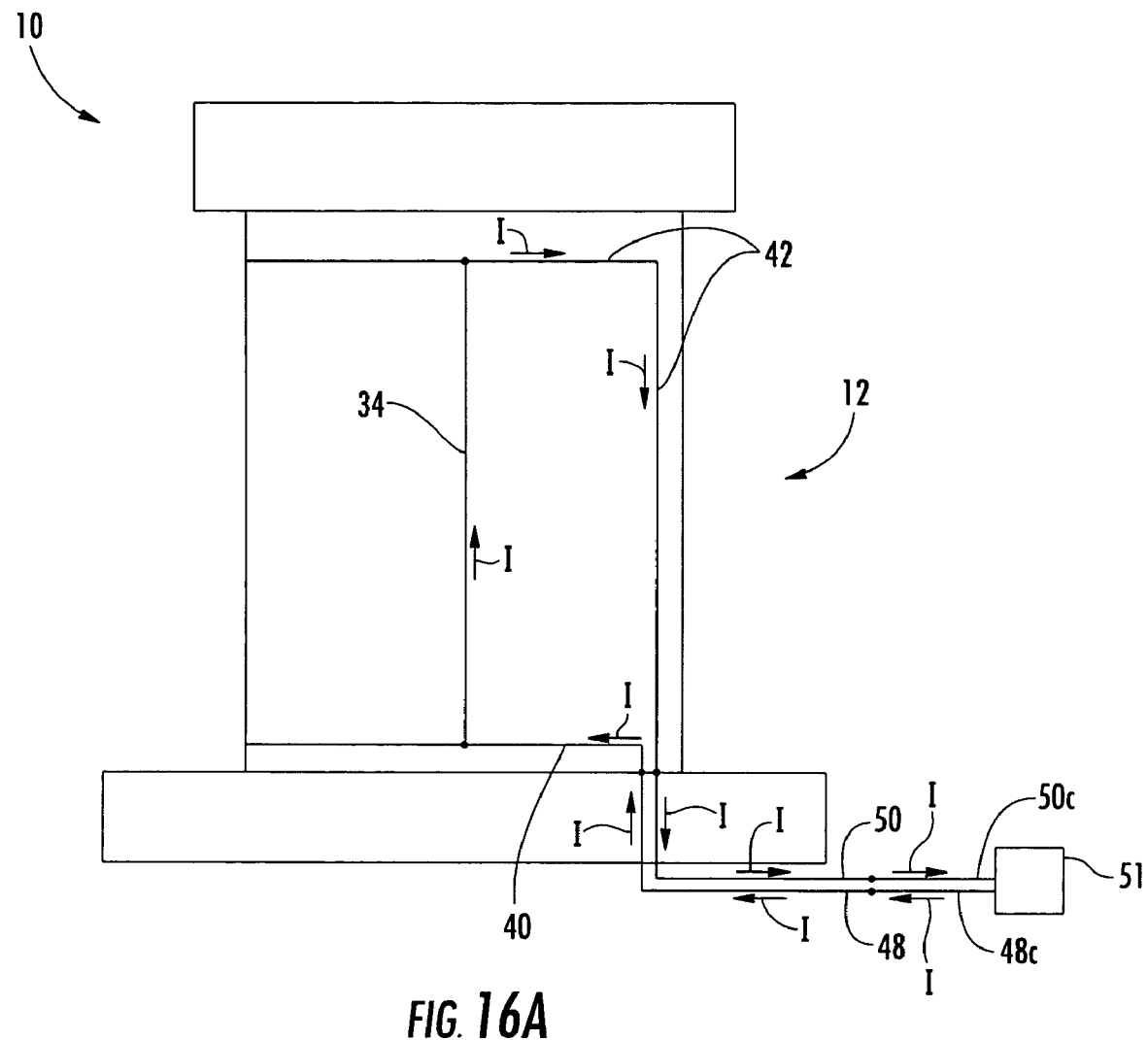
FIG. 16A is a side elevational view of a turbine vane according to aspects of the invention, showing one system for measuring resistance across an assessment wire.

Any of a number of techniques can be used to measure resistance. One manner of measuring resistance is shown in FIG. 16A. As shown, the first wire 40 can be electrically connected to the source wire 48, and the second wire 50 can be electrically connected to the source wire 42. Further, the source wires 48 and 50 can be electrically connected to wires 48c and 50c, respectively. Wires 48c and 50c can extend outside of the turbine. Wires 48c and 50c can be electrically connected to a controller 51. The controller 51 can include a current source as well as a voltage measuring device, such as any of those discussed above. Thus, the controller 51 can deliver current I to the assessment wire 34 by a conducting path formed by wires 48c, 48, 40. After passing along the assessment wire 34, the current I can return to the controller 51 by another conducting path formed by wires 42, 50, 50c. The resistance of the assessment wire 34, whether a single assessment or multiple wires (such as in the form of a net), can be determined by measuring the current I delivered by the controller 51 to the assessment wire 34 by wires 42, 50, 50c as well as wires 48c, 48, 40. In addition, voltage V can be measured across wires 48c and 50c at the controller 51. Thus, resistance can be determined by dividing the measured voltage V by the measured current I. In such case, the determined resistance includes the resistance of wires 48c, 48, 40, 50c as well as the assessment wire 34.

Figure 16B:
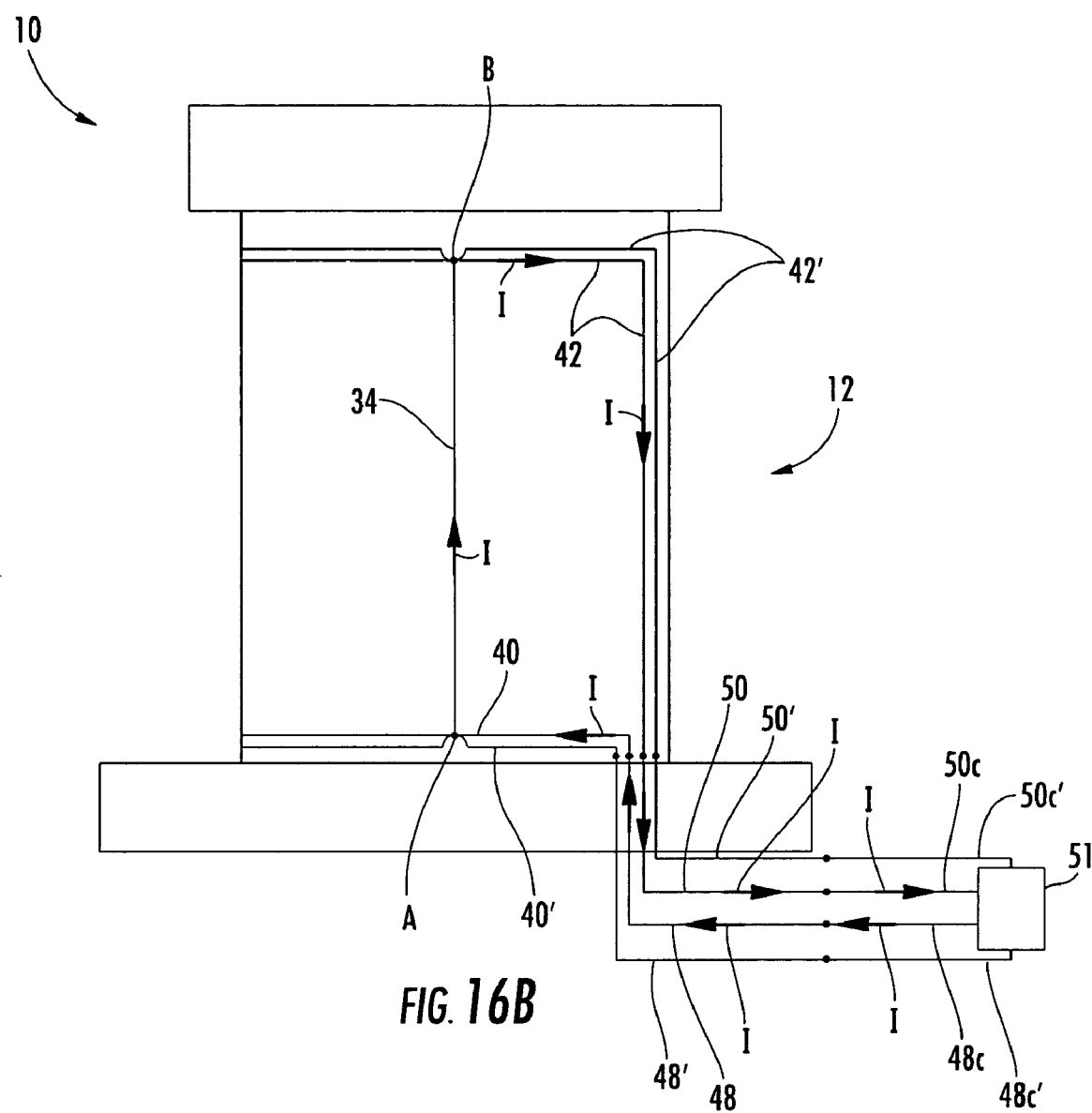
FIG. 16B is a side elevational view of a turbine vane according to aspects of the invention, showing another system for measuring resistance across an assessment wire.

A four point system for measuring resistance is shown in FIG. 16B. Again, the first wire 40 can be electrically connected to the source wire 48, and the second wire 42 can be electrically connected to the source wire 50. Further, the source wires 48 and 50 can be electrically connected to wires 48c and 50c, respectively. Wires 48c and 50c can extend outside of the turbine. Wires 48c and 50c can be electrically connected to a controller 51. The controller 51 can include a current source as well as a voltage measuring device, such as those discussed above. Additional wires 48c', 50c' can be electrically connected to the controller 51. Wires 48c', 50c' can be electrically connected with wires 48' and 50', respectively. Further, wires 40' and 42' can be provided on the vane 12 in any of the ways discussed above in connection with the first and second wires 40, 42. However, wires 40', 42' can be electrically insulated from the wires 40, 42. Further, the wires 40', 42' can be substantially parallel to the wires 40,42, but local deviations are possible. It should be noted that at one point, such as point B, the wire 42, the wire 42' and the assessment wire 34 can all be electrically connected. Likewise, the wires 40, 40' can be electrically connected with the assessment wire 34 at, for example, point A.

A conducting path formed by wires 40, 48, 48c can be substantially identical to a conducting path formed by wires 40', 48', 48c', but only the conducting path formed by 40, 48, 48c can be supplied with electrical current I from the controller 51. Similarly, a conducting path formed by wires 42, 50, 50c can be substantially identical to a conducting path formed by wires 42', 50', 50c'; however, only the conducting path formed by 42, 50, 50c can carry electrical current I. Thus, the conducting path formed by wires 40', 48' and 48c' and the conducting path formed by wires 42', 50', 50c' can be used by the controller 51 to measure voltage across the assessment wire 34. For a known current I, the resistance across the assessment wire 34 can be determined. It should be noted that, unlike the measurement system shown in FIG. 16A, voltage attributable to the resistance in the wires 40, 48, 48c, 42, 50, 50c is not measured. Thus, a more accurate determination of resistance across the assessment wire 34 can be achieved.

If provided, temperature readings from the thermocouple 58 can used to account for changes in the resistance across the assessment wires 34 attributable to temperature variations.

During engine operation, at least a portion of the thermal coating 30 can fail. The assessment wires 34 in the area of the damaged thermal coating 30 may also break, such as due to impact, wear or exposure to the high temperatures of the turbine. Whatever the cause, a disconnect in the assessment wires 34 or the first and second wires 40, 42 can disrupt current flow I between the first and second common wires 40, 42, which, in turn, can affect the resistance measured across the assessment wires 34.

Figure 14:
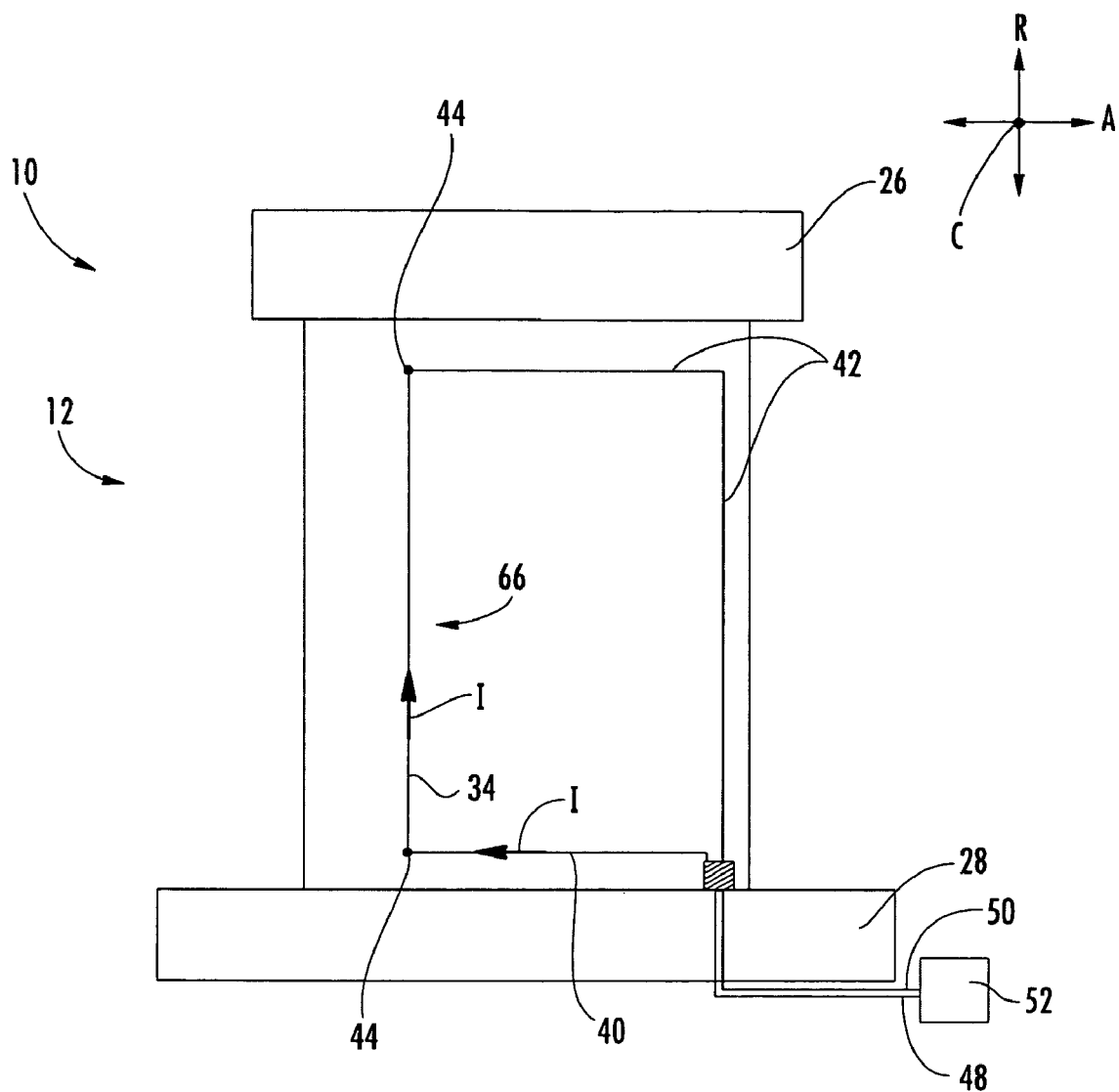
FIG. 14 is a side elevational view of a turbine vane according to aspects of the invention, showing a disconnect is a single assessment wire system.

The sensitivity of the response (that is, the change in resistance) can vary depending on the configuration of the wires 34, 40, 42. One relatively sensitive system can be any of the previously-discussed systems having a single assessment wire 34 connecting between the first and second wires 40, 42 (see, for example, FIGS. 5–7). Referring to FIG. 14, a break or a disconnect 66 at any point along the assessment wire 34 would reduce the current flow I between the first and second wires 40, 42 to zero, resulting in an infinite resistance being measured across the assessment wire 34. In such case, an operator would be alerted to a problem with a particular vane 10.

Figure 15:
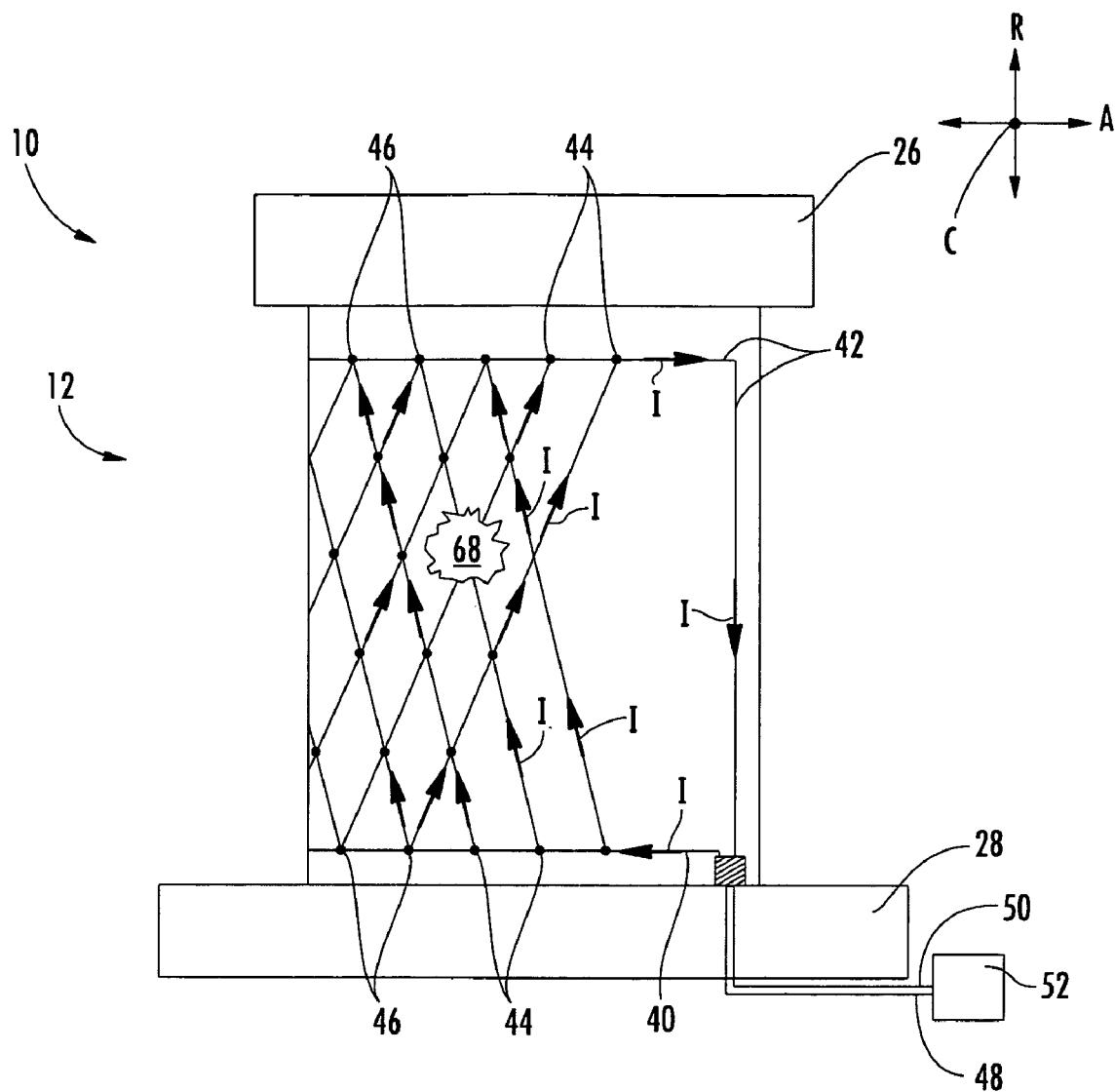
FIG. 15 is a side elevational view of a turbine vane according to aspects of the invention, showing a disconnect is a multiple assessment wire system.

A system according to aspects of the invention can be configured to provide a less sensitive response in the event of a disconnect. A less sensitive system can also provide general information as to the size and/or growth of damage in the thermal coating 30 in addition to a general awareness of a problem. For example, as shown in FIG. 15, damage causing a disconnect 68 in one or more of the assessment wires 34 would reduce but not halt the flow of current I from the first wire 40 to the second wire 42. The reduction in current flow I would lead to an increase in resistance, alerting an operator to a problem. Naturally, a large increase in resistance would indicate a greater the area of damage to the thermal coating 30. Any further increases in resistance can give an indication as to whether and how quickly damage is spreading. With this information, an operator can take corrective action, as needed, before a catastrophic failure forces a shut-down. In the case of assessment wires 34 provided in two or more layers, as discussed earlier, the depth of a penetration into the thermal coating 34 can be measured by monitoring for changes in resistance across each layer of thermal coating. Thus, corrective action can be taken if damage penetrates to a layer of assessment wires 34 that are provided at a critical depth.

Thus, it will be appreciated that a general assessment of the condition of a thermal coating 30 on a vane 10 can be evaluated while the turbine is on-line. Further, the system can facilitate inspection and repair by identifying the particular vanes 10 with thermal coating damage. Thus, if an off-line inspection is required, then not every vane needs to be inspected as must be done in current methods. Only those vanes having levels of damage that give rise to concern need be inspected. As a result, significant time, labor and cost savings can be realized.

The foregoing description is provided in the context of various systems for assessing the condition of a coating on a turbine vane during engine operation. While described in the contact of turbine vanes, it will be appreciated that aspects of the invention can be applied to other coated components in the hot gas path in a turbine engine including, for example, turbine blade and combustor liners. Thus, it will of course be understood that the invention is not limited to the specific details described herein, which are given by way of example only, and that various modifications and alterations are possible within the scope of the invention as defined in the following claims.

What is claimed is:

1. A system for monitoring the condition of a coating on a turbine engine component comprising:
   the turbine engine component;
   the coating applied aver at least a portion of the turbine engine component;
   a plurality of assessment wires extending about at least a portion of the component such that at least a portion of each assessment wire is in contact with the coating, wherein the plurality of assessment wires includes a first group of assessment wires and a second group of assessment wires, and wherein the first group of wires and the second group of wires are angled relative to each other such that each wire from the first group of wires crosses at least one wire from the second group of wires;
   a power source electrically connected to the plurality of assessment wires, wherein an electrical current is passed along the plurality of assessment wires; and
   a measuring device operatively associated with the plurality of assessment wires so as to determine the electrical resistance across plurality of assessment wires, whereby increases in resistance across the plurality of assessment wires indicate a disconnect in the at least one of the plurality of assessment wires which further indicates possible damage to the coating.

2. The system of claim 1 wherein the turbine engine component is an airfoil.

3. The system of claim 1 wherein the coating is a thermal barrier coating.

4. The system of claim 1 wherein the plurality of assessment wires is embedded within the coating.

5. The system of claim 1 further including a thermocouple provided in contact with at least the coating, wherein the thermocouple measures the temperature of at least the coating, whereby the temperature of the coating is used to discount changes in electrical resistance attributed to a change in temperature.

6. A system for monitoring the condition of a coating on an airfoil comprising:
   the airfoil having a radially inner end and a radially outer end, the airfoil defining an outer peripheral surface;
   a thermal coating substantially covering the outer peripheral surface of the airfoil;
   a plurality of assessment wires extending about at least a portion of the airfoil, wherein at least a portion of each assessment wire is in contact with the thermal coating;
   a power source electrically connected with the plurality of assessment wires, wherein an electrical current is passed along the plurality of assessment wires;
   a measurement device operatively associated with the plurality of assessment wires so as to determine the electrical resistance across the assessment wires, whereby increases in resistance across the assessment wires can provide information as to the size and growth of possible damage to the thermal coating.

7. The system of claim 6 further including:
   a first wire and a second wire operatively associated with the power source, wherein each of the plurality of assessment wires is electrically connected at one end to the first wire and at the other end to the second wire, wherein the first wire delivers the electrical current to each of the plurality of assessment wires and the second wire receives current from each of the assessment wires.

8. The system of claim 6 wherein the plurality of assessment wires is embedded in the thermal coating.

9. The system of claim 6 wherein the plurality of assessment wires is disposed beneath the thermal coating.

10. The system of claim 6 wherein the plurality of assessment wires is disposed over she thermal coating.

11. The system of claim 6 wherein at least one of the plurality of assessment wires is electrically insulated from the rest of the plurality of assessment wires.

12. The system of claim 6 wherein the plurality of wires is substantially equally spaced.

13. The system of claim 6 wherein the plurality of wires extends from near one radial end of the airfoil to near the opposite radial end of the airfoil.

14. The system of claim 6 wherein the plurality of wires extends substantially about the leading edge of the airfoil.

15. The system of claim 6 wherein the plurality of wires includes at least a first group of wires and a second group of wires, the first group of wires and the second group of wires are angled relative to each other such that each wire from the first group of wires crosses at least one wire from she second group of wires.

16. The system of claim 15 wherein the first and second groups of wires are electrically connected at at least some of the crossing points therebetween.

17. A method of on-line evaluation of the condition of a coating on an airfoil comprising:
   providing a turbine engine including the airfoil with an outer peripheral surface that is at least partially covered with a thermal coating, wherein at least one assessment wire extends about at least a portion of the outer peripheral surface of the airfoil such that at least a portion of each assessment wire is in contact with the coating;
   providing a power source that is operatively connected to the at least one assessment wire, wherein the at least one assessment wire continuously receives the electrical current from the power source;
   determining resistance across the at least one assessment wire; and
   monitoring changes in resistance across the at least one assessment wire, whereby an increase in the resistance across the at least one assessment wire indicates a general assessment of the condition of the, thermal coating.

18. The method of claim 17 wherein the step of determining is conducted on a substantially continuous basis.

19. The method of claim 17 wherein the and at least one assessment wire continuously receives the electrical current during engine operation wherein the determining step is performed during engine operation.

* * * * *